US008727199B2

(12) United States Patent
Wenchell

(10) Patent No.: US 8,727,199 B2
(45) Date of Patent: *May 20, 2014

(54) SURGICAL STAPLER

(75) Inventor: Thomas Wenchell, Durham, CT (US)

(73) Assignee: Covidien LP, Mansfield, MA (US)

( * ) Notice: Subject to any disclaimer, the term of this patent is extended or adjusted under 35 U.S.C. 154(b) by 256 days.

This patent is subject to a terminal disclaimer.

(21) Appl. No.: 12/335,732

(22) Filed: Dec. 16, 2008

(65) Prior Publication Data

US 2009/0173766 A1 Jul. 9, 2009

Related U.S. Application Data

(60) Provisional application No. 61/018,685, filed on Jan. 3, 2008.

(51) Int. Cl.
*A61B 17/10* (2006.01)
*A61B 17/04* (2006.01)

(52) U.S. Cl.
USPC ...................................................... 227/178.1

(58) Field of Classification Search
CPC ............... A61B 17/07207; A61B 2017/07278
USPC ....................... 227/175.1–182.1, 19; 606/219
See application file for complete search history.

(56) References Cited

U.S. PATENT DOCUMENTS

| 4,767,044 | A | * | 8/1988 | Green | 227/19 |
| 4,801,948 | A | | 1/1989 | Kato | |
| 4,941,623 | A | * | 7/1990 | Pruitt | 227/19 |
| 6,202,914 | B1 | | 3/2001 | Geiste et al. | |
| 6,978,922 | B2 | * | 12/2005 | Bilotti et al. | 227/180.1 |
| RE39,841 | E | * | 9/2007 | Bilotti et al. | 227/180.1 |
| 7,398,908 | B2 | * | 7/2008 | Holsten et al. | 227/176.1 |
| 7,401,721 | B2 | * | 7/2008 | Holsten et al. | 227/176.1 |
| 7,588,174 | B2 | * | 9/2009 | Holsten et al. | 227/176.1 |
| 7,604,151 | B2 | * | 10/2009 | Hess et al. | 227/181.1 |
| 7,635,074 | B2 | * | 12/2009 | Olson et al. | 227/176.1 |
| 7,669,746 | B2 | * | 3/2010 | Shelton, IV | 227/175.1 |
| 7,673,781 | B2 | * | 3/2010 | Swayze et al. | 227/175.1 |
| 7,726,538 | B2 | * | 6/2010 | Holsten et al. | 227/176.1 |

(Continued)

FOREIGN PATENT DOCUMENTS

| EP | 1857057 | 11/2007 |
| JP | 61-98250 | 7/1994 |
| JP | 9-164144 | 6/1997 |
| JP | 2007-307373 | 11/2007 |

OTHER PUBLICATIONS

Japanese Official Action in corresponding JP Appln. No. 2008-334445, dated Mar. 12, 2013, with the English translation; (9 pages).

*Primary Examiner* — Robert Long

(57) ABSTRACT

A surgical fastener applying apparatus comprising a cartridge section having a cartridge containing a plurality of fasteners, an anvil section having an anvil for receiving the fasteners when advanced from the cartridge, the cartridge and anvil sections clamping tissue therebetween. The first and second cam members are movable within the cartridge section to fire the fasteners. A cam member supporting member fixed within the cartridge section has an upper surface on which the cam members are slidable. The upper surface of the cam member supporting member has a first upper surface portion on a first plane and a second lower surface portion in a different substantially parallel second plane such that the first and second cam members slide in offset planes on the upper surface to fire the fasteners.

15 Claims, 6 Drawing Sheets

(56) References Cited

U.S. PATENT DOCUMENTS

| | | | |
|---|---|---|---|
| 7,726,539 B2* | 6/2010 | Holsten et al. | 227/179.1 |
| 7,753,249 B2* | 7/2010 | Sonnenschein et al. | 227/176.1 |
| 8,403,198 B2* | 3/2013 | Sorrentino et al. | 227/180.1 |
| 2005/0189397 A1* | 9/2005 | Jankowski | 227/176.1 |
| 2007/0045379 A1* | 3/2007 | Shelton | 227/176.1 |
| 2007/0131732 A1* | 6/2007 | Holsten et al. | 227/179.1 |
| 2007/0194079 A1 | 8/2007 | Hueil et al. | |
| 2007/0194081 A1* | 8/2007 | Hueil et al. | 227/176.1 |
| 2007/0262116 A1* | 11/2007 | Hueil et al. | 227/175.1 |
| 2008/0164297 A1* | 7/2008 | Holsten et al. | 227/176.1 |
| 2008/0272175 A1* | 11/2008 | Holsten et al. | 227/178.1 |
| 2009/0261144 A1* | 10/2009 | Sniffin et al. | 227/176.1 |
| 2009/0277947 A1* | 11/2009 | Viola | 227/176.1 |
| 2009/0277948 A1* | 11/2009 | Beardsley et al. | 227/178.1 |
| 2009/0321496 A1* | 12/2009 | Holsten et al. | 227/180.1 |
| 2010/0032470 A1* | 2/2010 | Hess et al. | 227/176.1 |
| 2010/0108739 A1* | 5/2010 | Holsten et al. | 227/176.1 |
| 2010/0127043 A1* | 5/2010 | Olson et al. | 227/178.1 |
| 2010/0200641 A1* | 8/2010 | Holsten et al. | 227/180.1 |
| 2013/0037596 A1* | 2/2013 | Bear et al. | 227/176.1 |

* cited by examiner

SURGICAL STAPLER

This application claims priority from provisional application Ser. No. 61/018,685, filed Jan. 3, 2008, the entire contents of which are incorporated herein by reference.

BACKGROUND

1. Technical Field

The present disclosure relates to a surgical stapling device and more particularly to a surgical stapling device having pusher-engaging cam members that are slidable on offset planes.

2. Background of the Related Art

There are several known types of surgical stapling instruments specifically adapted for use in various procedures. In many such surgical devices, tissue is first grasped or clamped between opposing jaw structures and then joined by surgical fasteners. The fasteners are typically in the form of surgical staples. These staples generally include a pair of legs adapted to penetrate tissue and connected by a backspan from which they extend. In use, the staples are formed to a "B" configuration. Two-part fasteners are also known and include legs that are barbed and connected by a backspan which are engaged and locked into a separate retainer piece that is usually located in the anvil. In some devices, a knife is provided to cut the tissue which has been joined by the fasteners.

In these devices, one of the jaw structures carries a staple cartridge having one or more laterally spaced rows of staples, which are aligned with corresponding rows of anvil depressions on an opposing jaw structure. The tissue is initially gripped or clamped such that individual fasteners can be ejected from the cartridge, through the slots, and forced through the clamped tissue. The staples are ejected by longitudinal movement of a driver and forced through the clamped tissue, forming against the staple forming depressions of the anvil. The staples can be arranged in a linear or non-linear row.

A common issue in transecting tissue and/or in anastomosis procedures employing the surgical stapling instruments is the balance between anastomotic strength and the degree of hemostasis achievable. It is known to include different size staples in a surgical stapling instrument having a constant gap (uniform distance) between an anvil and a staple cartridge.

A common concern in these surgical procedures is hemostasis, or the rate at which bleeding of the target tissue is stopped. It is commonly known that by increasing the amount of pressure applied to a wound, the flow of blood can be limited, thereby decreasing the time necessary to achieve hemostasis. To this end, conventional surgical fastening apparatus generally apply two or more rows of fasteners about the cut-line to compress the surrounding tissue in an effort to stop any bleeding and to join the cut tissue together. Each of the fasteners will generally apply a compressive force to the tissue sufficient to effectuate hemostasis, however, if too much pressure is applied, this can result in a needless reduction in blood flow to the tissue surrounding the cut-line. Accordingly, the joining of tissue together in this manner may result in an elevated level of necrosis, a slower rate of healing, and/or a greater convalescence. On the other hand, if not enough pressure is applied, proper hemostasis may not be achieved.

Consequently, it would be advantageous to provide a surgical fastening apparatus capable of limiting the flow of blood in the tissue immediately adjacent the cut tissue to effectuate hemostasis and wound closure, while maximizing blood flow in the surrounding tissue to facilitate healing.

SUMMARY

The present disclosure relates to forming different sized staples by advancing cam members on different planes. In preferred embodiments, the cam members have common sizes and angles and the pushers have common sizes and angles which among other advantages, can facilitate the manufacturing process.

More specifically, a cartridge section having offset or stepped surfaces for cam members to travel along is disclosed herein. The offset or stepped surfaces allow the cam members to travel in different planes, which enables in preferred embodiments cam members of substantially the same height and pushers of substantially the same height to be used to fire staples of different sizes against an anvil.

In one aspect, the present disclosure provides a surgical fastener applying apparatus comprising a cartridge section having a cartridge containing a plurality of fasteners and an anvil section having an anvil for receiving the fasteners when advanced from the cartridge, the cartridge and anvil sections clamping tissue therebetween. First and second cam members are movable within the cartridge section to fire the fasteners. A cam member supporting member is fixed within the cartridge section and has an upper surface on which the cam members are slidable. The upper surface of the cam member supporting member has a first upper surface portion on a first plane and a second lower surface portion on a different substantially parallel second plane such that the first and second cam members slide in offset planes on the upper surface to fire the fasteners.

In a preferred embodiment, the first and second cam members are of substantially the same height. In a preferred embodiment, the plurality of fasteners include a first set of fasteners having legs of a first length and a second set of fasteners having legs of a second longer length.

In a preferred embodiment, the first upper surface portion is closer to the anvil section than the second lower surface portion, and the second cam member slides along the second lower surface to fire the second set of fasteners.

The cartridge may include third and fourth cam members, the third and fourth cam members being movable on substantially parallel offset planes. The second and fourth cam members are preferably positioned outboard of the first and third cam members and configured to fire fasteners having a length greater than a length of fasteners fired by the first and third cam members.

In one embodiment, the cartridge includes a plurality of fastener pushers configured to engage the fasteners as they are advanced by the cam members, the fastener pushers preferably being of substantially the same height. The pushers are preferably movable by the cam members in a direction substantially transverse to the direction of movement of the cam members.

The present disclosure also provides a surgical fastener applying apparatus comprising a cartridge section having a cartridge containing first and second sets of fasteners and an anvil section having an anvil for receiving the fasteners when advanced from the cartridge, the cartridge and anvil sections clamping tissue therebetween. A first cam member is movable within the cartridge section to advance the first set of fasteners against the anvil to fully form the fasteners, the first cam member movable in a first plane. A second cam member is movable within the cartridge section along with the first cam member to advance the second set of fasteners to fully form the fasteners, the second cam member movable in a second plane offset from the first plane and further from the anvil section than the first plane when the anvil and cartridge sections are positioned to clamp tissue therebetween.

In one embodiment the cam members are of substantially the same height. In one embodiment, the first set of fasteners has legs of a first length and the second set of fasteners has legs of a second longer length.

Preferably, the cartridge includes a plurality of fastener pushers configured to engage the fasteners as they are advanced by the cam members, the fastener pushers preferably being of substantially the same height.

BRIEF DESCRIPTION OF THE DRAWINGS

Various embodiments of the present disclosure are described hereinbelow with references to the drawings, wherein.

DETAILED DESCRIPTION OF EMBODIMENTS

Embodiments of the presently disclosed stapler will now be described in detail with reference to the drawings wherein like numerals designate identical or corresponding elements in each of the several views. As is common in the art, the term "proximal" refers to that part or component closer to the user or operator, i.e. surgeon or physician, while the term "distal" refers to that part or component further away from the user.

Figure 1:
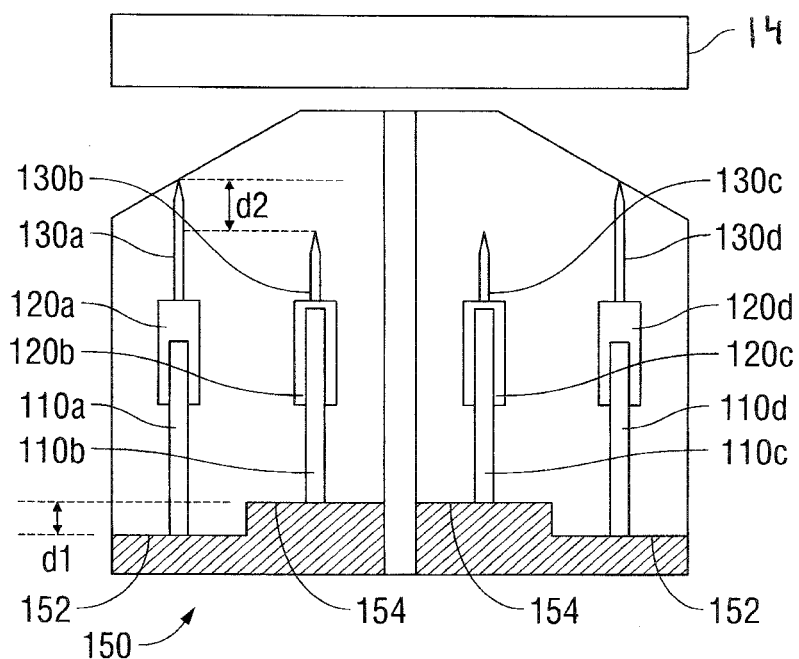
FIG. 1 is a view in partial cross-section showing the cams bars on different planes.
Figure 2:
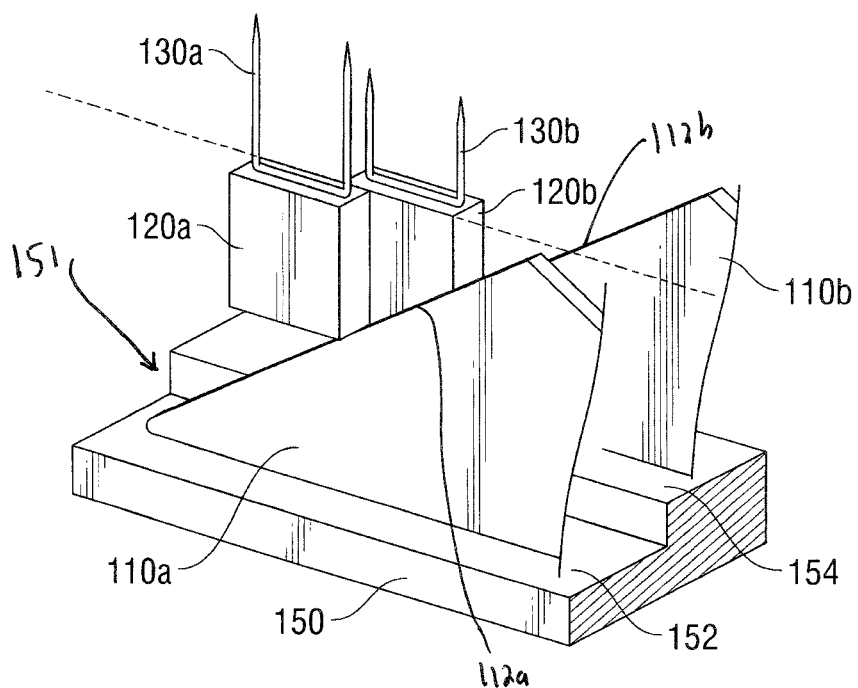
FIG. 2 is a perspective view of two cam bars and two staple pushers of FIG. 1.
Figure 3:
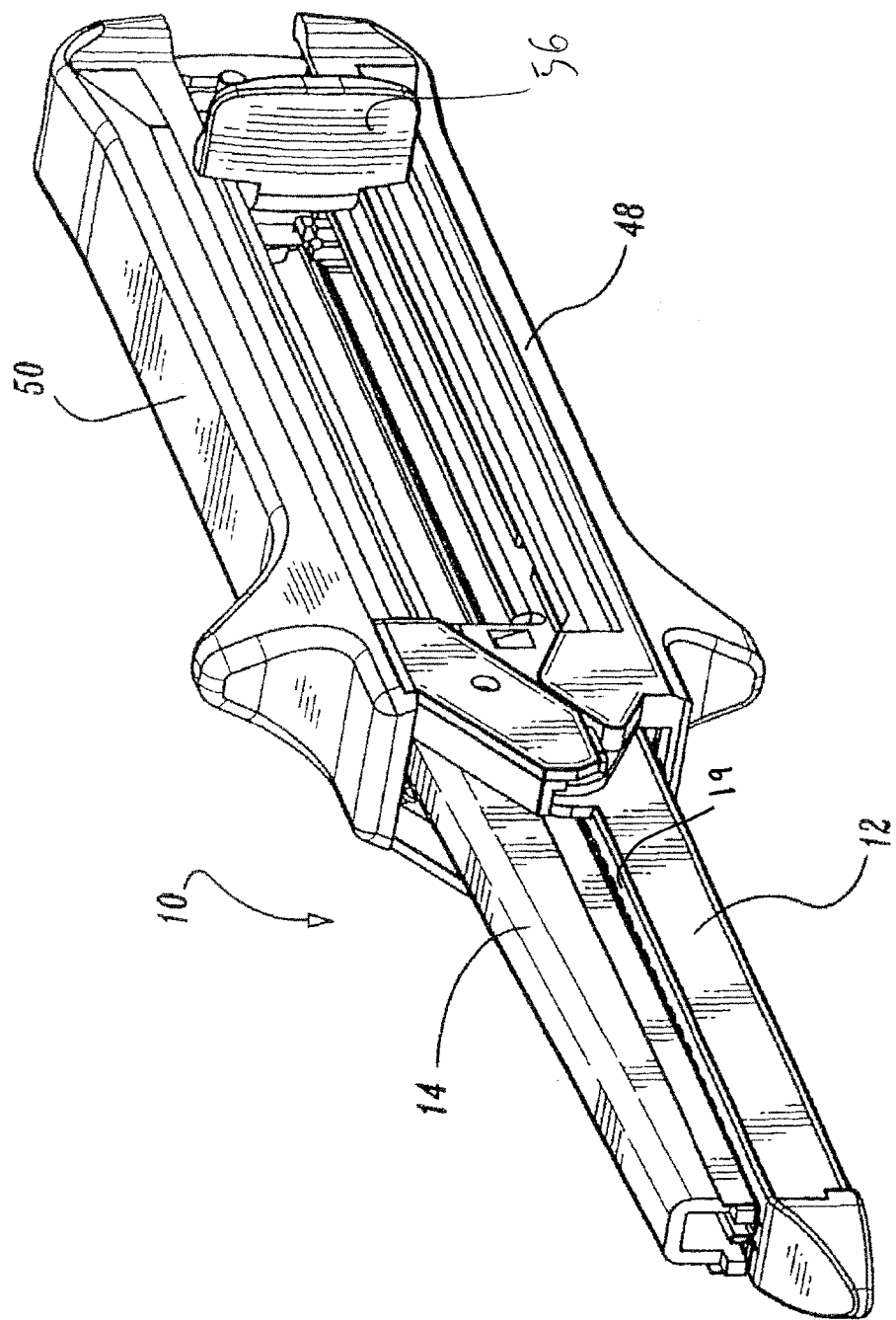
FIG. 3 is a perspective view of one embodiment of a surgical stapler having the offset cam bars of FIG. 1.
Figure 4:
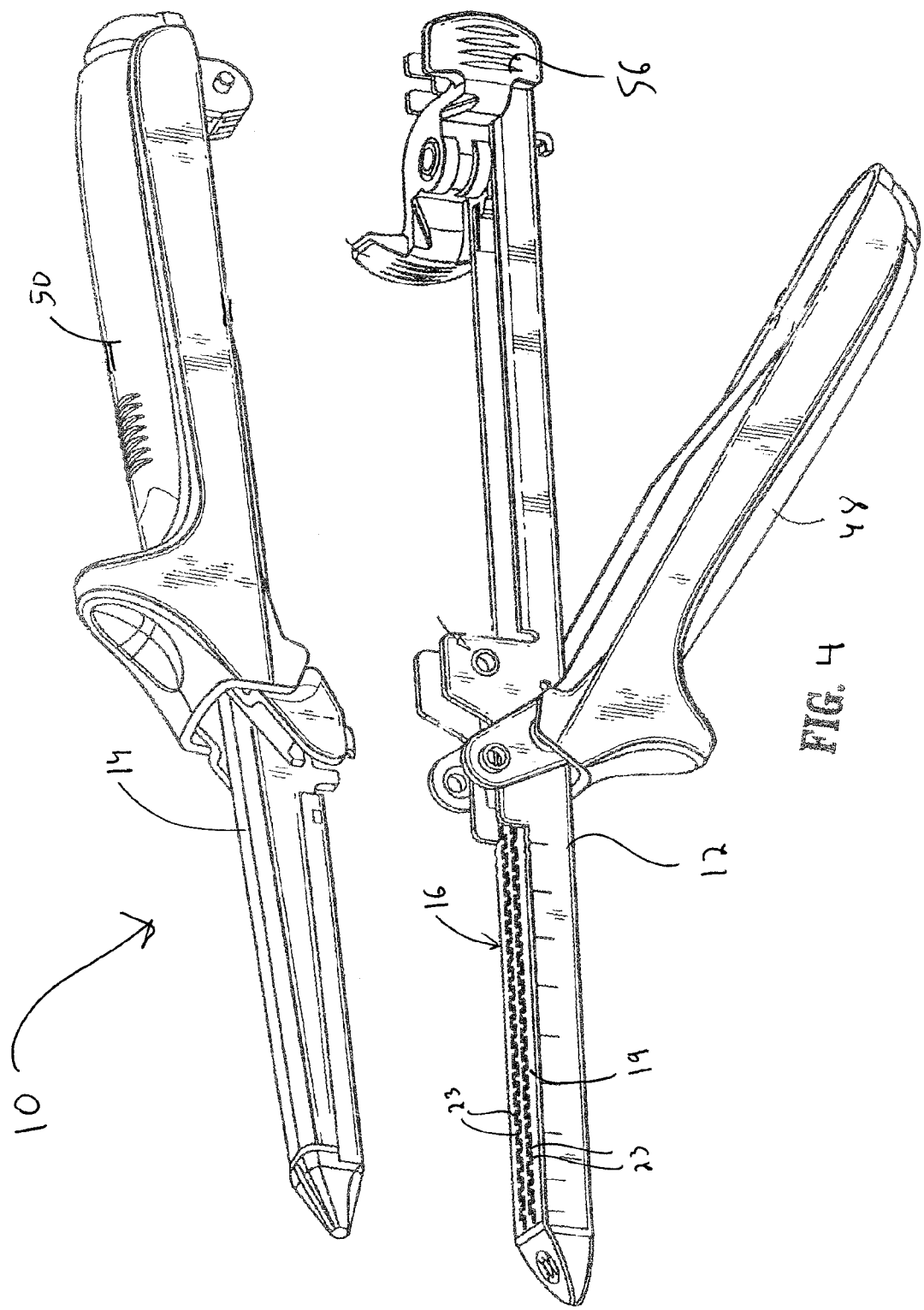
FIG. 4 is a perspective view of the surgical stapler of FIG. 3 with the anvil and cartridge assemblies separated.

FIGS. 1 and 2 illustrate a first embodiment of the cam bar/pusher arrangement of the present disclosure. FIGS. 3 and 4 illustrate one type of surgical stapler that can incorporate the cam bar/pusher arrangement of FIG. 1.

Figure 2A:
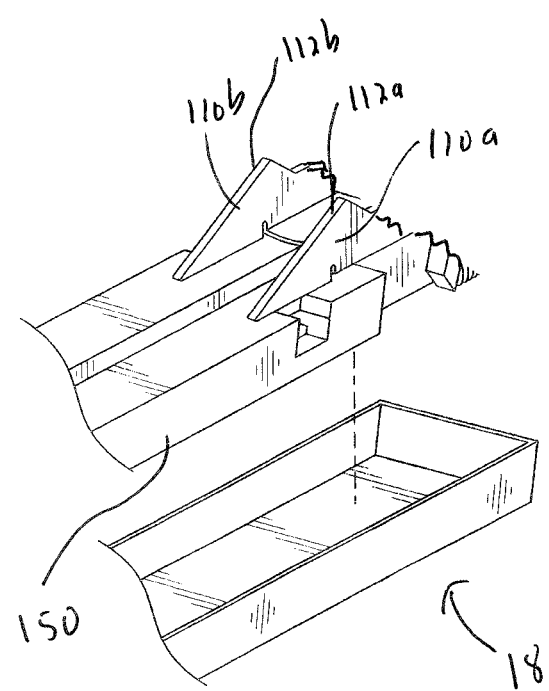
FIG. 2A is a perspective view of a portion of the cam bars and cam bar support separated from the supporting channel.

Turning first to FIGS. 3 and 4, the stapler 10 has a cartridge receiving half section 12, an anvil half section 14, and handles 48 and 50 for facilitating clamping of the sections 12 and 14. Cartridge half section 12 has a channel 18 (FIG. 2A) to receive cartridge assembly 16 which includes a plurality of staples 130 and a plurality of pushers 120 to advance the staples 130 from the cartridge 19 through slots 23. A cam bar assembly is advanced by distal advancement of manual firing lever 56. The cam bar assembly is slidable on cam bar supporting member 150 for longitudinal advancement in the cartridge 19 to advance the pushers 120 in a direction substantially transverse to the longitudinal axis of the stapler and substantially transverse to the direction of movement of the cam bars. Engagement of the pushers 120 by the cam members advances the staples 130 through the tissue and into contact with the anvil depressions of the anvil half section 14. Preferably there are two staggered rows of slots 23 formed on either side of a slotted knife track in the cam bar assembly which guides a knife between the rows of staples. A single staple is positioned in each of the slots 23. Staple pushers 120 are aligned with each slot 23 so that a single staple pusher is positioned under the staple retained in the slot. The pushers can optionally be attached to each other in groups of two offset oriented pusher pairs. More details of the stapler are disclosed in commonly assigned U.S. Pat. No. 7,140,527, issued Nov. 28, 2006, and U.S. Pat. No. 7,055,730, issued Jan. 6, 2006, the entire contents of each of these applications is incorporated herein by reference.

With reference to FIGS. 1 and 2 illustrating the cam member arrangement of the present disclosure, the pushers 120 are advanced by the camming surfaces 112a, 112b of cam members 110a, 110b which as shown are in the form of cam bars 110a, 110b. FIG. 2 illustrates a distal portion of two of the cam bars 110, 110b and two of the pushers 120a, 120b; FIG. 1 illustrates four cam bars (110a-110d) and four of the pushers 120a-120d. The camming surfaces 112a, 112b are preferably longitudinally staggered with respect to each other to distribute the firing forces More specifically, four cam bars (members) 110a-110d, four pushers 120a-120d and four staples 130a-130d are shown in FIG. 1. The cam bars 110a-110d are preferably of substantially the same size (height) and angle. The staple pushers 120a-120d are also preferably of substantially the same size (height). Cartridge half section 12 also includes a cam bar (member) supporting member 150 fixedly mounted within channel 18 and having an offset plane 151 on its upper surface. The upper surface includes a lower surface portion 152 and a substantially parallel upper surface portion 154 on each side of the longitudinal centerline and which form surfaces on which the respective cam bars (members) 110a-110d slide distally to sequentially fire a longitudinal row of staples contained in the staple cartridge 19. As shown, cam bar 110a is positioned on (and slidable longitudinally along) lower surface portion 152 of offset plane 151 and is in contact with pusher 120a, which contacts staple 130a. Cam bar 110b is positioned on (and slidable longitudinally along) upper surface portion 154 of offset plane 151 and is in contact with pusher 120b, which contacts staple 130b. Similar to cam bar 110b, cam bar 110c is positioned on upper surface portion 154; similar to cam bar 110a, cam bar 110d is positioned on lower surface portion 152 to contact respective pushers 120c, 120d to fire staples 130c, 130d. Thus, cam bars 110a and 110d are outboard of cam bars 110b, 110c.

As can be appreciated with reference to the Figures, the difference in heights of surface portions 152, 154 of offset plane 151 enables staples 130 of different sizes (leg lengths) to be fired into anvil pockets of anvil assembly 14 (shown schematically in FIG. 1) for formation by the anvil. Accordingly, the staples of smaller sizes (130b and 130c) are aligned with cam bars 110b and 110c, respectively, on upper surface portion 154. The staples of larger sizes (130a and 130d) are aligned with cam bars 110a and 110d, respectively, on lower surface portion 152. It is envisioned in a preferred embodiment that the height difference "d1" between surface portions 152 and 154 of offset plane 151 is approximately twice the height difference "d2" between larger staples (130a and 130d) and smaller staples (130b and 130c). Other height differences are also contemplated. Preferably, the smaller staples are in the inside rows and the larger staples are in the outside rows. In this manner, the longer staples are provided on the outer rows where the tissue might be thicker as a result of clamping by the instrument jaws (anvil and cartridge) as some of the fluid of the tissue is squeezed out so that the tissue is compressed further at the center portions of the cartridge and anvil than at the lateral edges, thereby leaving thicker tissue at the edges. In this manner, the stapler is capable of limiting the flow of blood in the tissue immediately adjacent the cut tissue to effectuate hemostasis and wound closure, while maximizing blood flow in the surrounding tissue to facilitate healing.

It should be appreciated that the offset planes of the present disclosure can also be used with other staplers, including, for example, other linear staples and endoscopic linear staplers, such as disclosed for example in FIG. 5 described below.

It is also contemplated that as an alternative to two surface heights of the cam member support 150 (or support 240 described below), more than two surface heights can be used. For instance, the offset planes can include surfaces of three different heights to provide advancement of cam members at three different levels. This can be used, for example, for applying three different size staples.

A method of firing staples of different sizes is also provided. The method includes causing first and third cam members (bars) 110b, 110c to travel along a first plane and causing second and fourth cam members (bars) 110a, 110d, outboard of the first and third cam members 110b, 110c, to travel along a second plane, where the first plane and the second plane are offset from each other. The second plane is further from the anvil surface when the cartridge 19 and anvil are in position clamping tissue therebetween. As the cam bars 110a-110d travel along the upper surface of cam member support 150, they contact respective pushers which then drive the respective staples out of the corresponding cartridge slot, through tissue clamped between the anvil and cartridge, and into anvil pockets for formation into B-shaped staples. This method applies staples of different lengths. For example, staples of shorter length would be applied to clamped tissue closer to the center of the jaws and staples of longer length would be applied to clamped tissue further from the center.

In a preferred embodiment, the raised (stepped) surfaces for supporting the cam bars can be formed on a plastic or other material insert in the bottom of channel 18 of the cartridge half section 12. The insert can be one piece formed with surfaces on different planes, e.g. by varying the thickness of the portions, or, alternatively, separate inserts to achieve the differing heights can be utilized.

Figure 5:
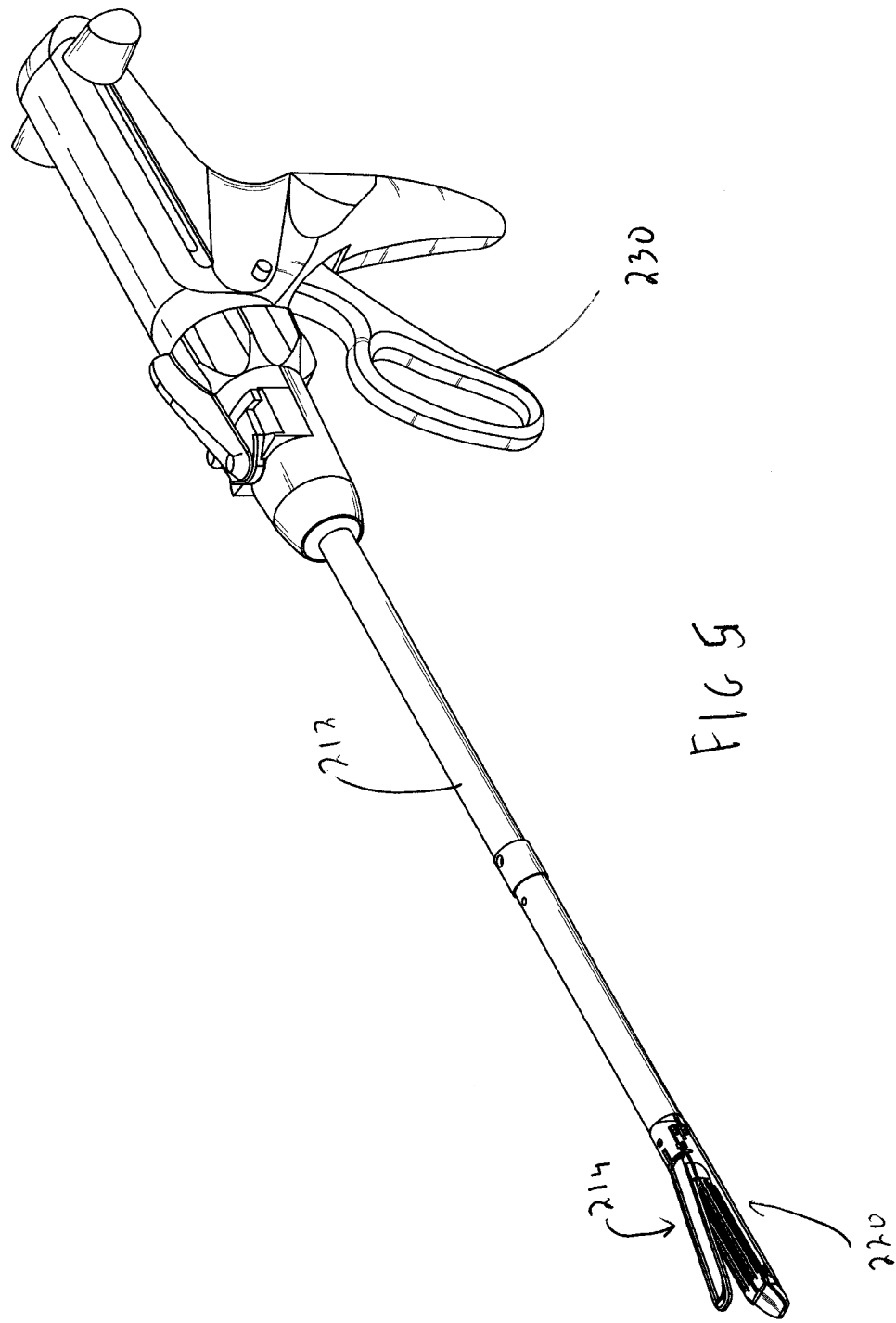
FIG. 5 is a perspective of an alternate embodiment of a surgical stapler of the present disclosure having offset camming members.
Figure 6:
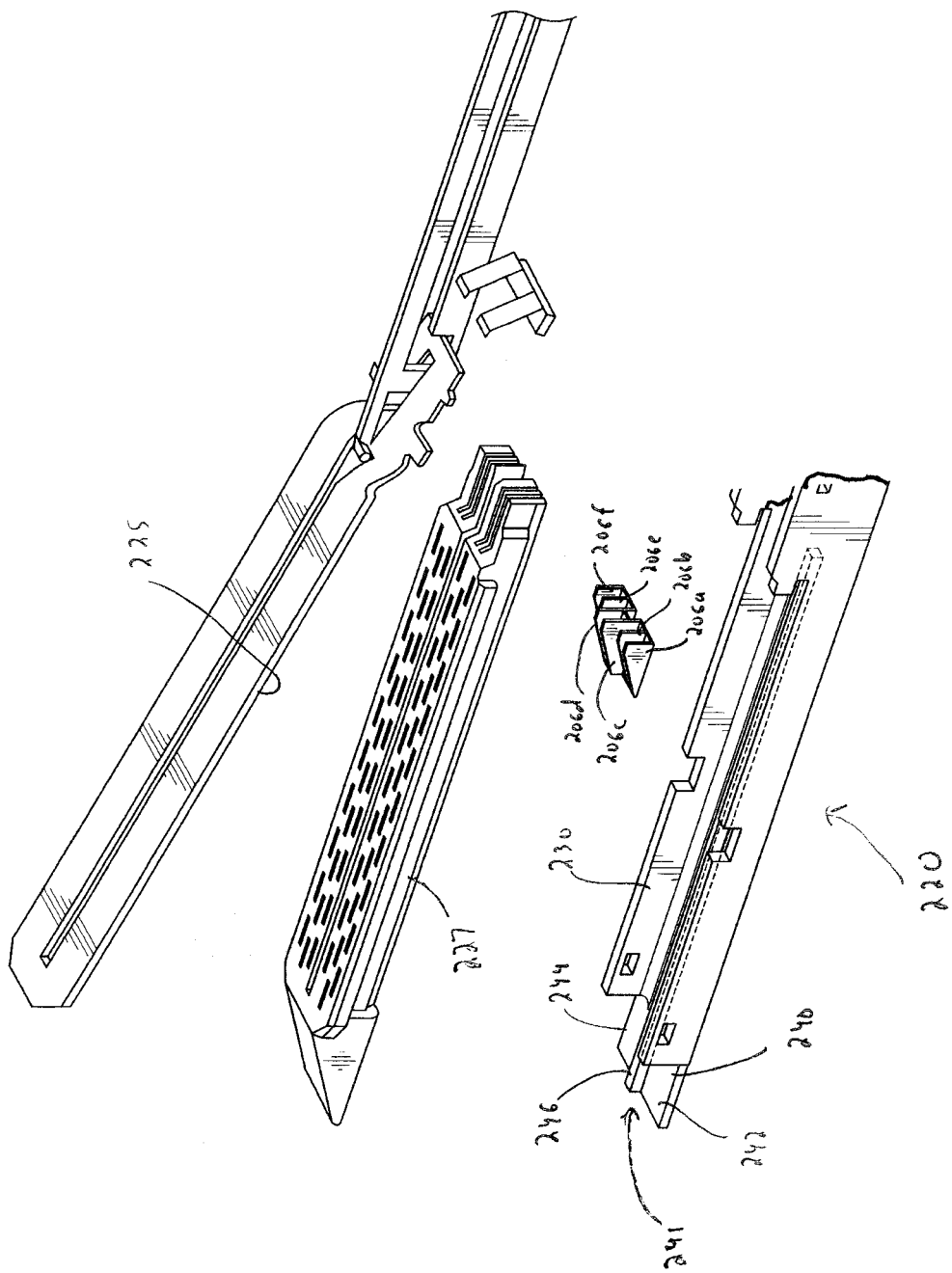
FIG. 6 is an exploded perspective view of the distal portion of the surgical stapler of FIG. 5.

FIGS. 5 and 6 illustrate an alternate embodiment utilizing the concept of cam members on offset planes. Six camming members 206a-206e are illustrated, attached together, with the two outer cam members on each side advanceable along one plane and the two middle cam members advanceable along a higher plane. More specifically, camming members 206a, 206b, 206e and 206f form the two outer rows of the cam bar assembly on each side of a longitudinal axis of the assembly. Cam members 206c and 206d are positioned in the middle (between the two outer rows) and configured for firing the two inner rows of staples. A cam member support 240 has an upper surface with an offset plane 241 such that it is stepped as shown to provide substantially parallel offset planes to offset the height of the two inner cam members 206c, 206d from the four outer cam members 206a, 206b, 206e, 206f. More specifically, cam member supporting member 240 is fixedly positioned within channel 230 of cartridge assembly 220 and its upper surface includes first and second lower surface portions 242, 244, and an intermediate upper surface portion 246 in between. The intermediate surface portion 246 has a raised surface such that it is higher, e.g. closer to the anvil assembly 214 when the instrument is clamped, than the outer lower surface portions 242, 244. The higher positioned cam members 206c, 206d slide along the raised intermediate surface portion 246. The cam bars slide distally to sequentially advance staple pushers in a direction substantially transverse to the movement of the cam members 206a-206f to fire longitudinal rows of staples contained in cartridge 227 through the tissue and against anvil member 225 to form the staples. In a preferred embodiment, the staples having legs of shorter length are fired by intermediate cam members 206c, 206d and the larger staples having legs of longer length are fired by the outer set of cam members 206a, 206b, 206e, and 206f. The outer surface portions 242 and 244 of offset plane 241 are lower, e.g. further from the anvil assembly 214 when the instrument is clamped, to accommodate the outer cam members 206a, 206b, 206e, 206f to fire staplers of longer length than the length of the staples in the inner rows.

This cam arrangement can be used with the endoscopic surgical stapler of FIG. 5, which has an elongated tubular portion 212, an anvil assembly 214 pivotally mounted at a distal end portion of the elongated tubular portion 212 and a cartridge assembly 220. The anvil and cartridge assemblies 214, 220 are moved into approximation to clamp tissue therebetween. A handle 230 is squeezed to clamp the anvil and fire the staples in the manner disclosed in U.S. Pat. No. 5,762,256 issued Jun. 9, 1998 and U.S. Pat. No. 5,865,361 issued Feb. 2, 1999, the entire contents of which are incorporated herein by reference.

In a preferred embodiment, staples of longer leg length are placed in the four outer rows and staples of shorter leg length are placed in the two inner rows. Preferably, the cam members are of substantially the same height, as are the pushers.

Although described for fastener applying apparatus for firing staples formed by an anvil, the offset plane of this disclosure could also be used in fastener applying apparatus for firing two part fasteners.

While the above description contains many specifics, these specifics should not be construed as limitations on the scope of the present disclosure, but merely as illustrations of various embodiments thereof. Therefore, the above description should not be construed as limiting, but merely as exemplifications of various embodiments. Those skilled in the art will envision other modifications within the scope and spirit of the disclosure.

What is claimed is:

1. A surgical fastener applying apparatus comprising
a cartridge section having a cartridge containing a plurality of fasteners and a plurality of fastener pushers;
an anvil section having an anvil for forming the plurality of fasteners when advanced from the cartridge, the cartridge and anvil sections configured for clamping tissue therebetween;
first and second cam bars movable within the cartridge section to fire the plurality of fasteners; and
a cam bar supporting member fixed within the cartridge section and having an upper surface, the first and second cam bars slidable along the upper surface, the upper surface of the cam bar supporting member having a first upper surface portion on a first plane and a second lower surface portion in a second plane oriented parallel in relation to the first plane such that the first and second cam bars slide in offset planes on the upper surface to fire the plurality of fasteners, wherein the first and second cam bars are of substantially the same height and an overall height of the cam bar on the first upper surface portion in the first plane is greater that an overall height of the cam bar on the second lower surface portion in the second plane,
wherein prior to firing, the plurality of fastener pushers are spaced apart from each of the first upper surface portion and second lower surface portion to engage the first and second cam bars, and wherein the plurality of fastener pushers spaced apart from the first upper surface portion have a height that is equal to a height of the plurality of fastener pushers spaced apart from the second lower surface portion.

2. The surgical fastener applying apparatus of claim 1, wherein the plurality of fasteners include a first set of fasteners having legs of a first length and a second set of fasteners having legs of a second longer length.

3. The surgical fastener applying apparatus of claim 2, wherein the first upper surface portion is closer to the anvil section than the second lower surface portion, the second cam bar slides along the second lower surface to fire the second set of fasteners.

4. The surgical fastener applying apparatus of claim 1, wherein the cartridge includes third and fourth cam bars, the second and fourth cam bars being movable on offset planes, the second and fourth cam bars positioned outboard of the first and third cam bars.

5. The surgical fastener applying apparatus of claim 1, wherein the second and fourth cam bars are configured to tire fasteners having a length greater than a length of fasteners fired by the first and third cam bars.

6. The surgical fastener applying apparatus of claim 1, wherein the first and second upper surface portions are formed by varying a thickness of the cam bar supporting member.

7. The surgical fastener applying apparatus as recited in claim 1, wherein the plurality of fastener pushers are configured to engage the plurality of fasteners as they are advanced by the cam bars.

8. The surgical fastener applying apparatus as recited in claim 7, wherein the first and second cam bars are of substantially the same height.

9. The surgical fastener applying apparatus of claim 7, wherein the plurality of pushers are movable by the cam bars in a direction substantially transverse to the direction of movement of the cam bars.

10. The surgical fastener applying apparatus of claim 9, wherein the first and second cam bars are attached and move as a single unit.

11. A surgical fastener applying apparatus comprising
a cartridge section having a cartridge containing first and second sets of fasteners and a plurality of fastener pushers;
an anvil section having an anvil for forming the first and second fasteners when advanced from the cartridge, the cartridge and anvil sections clamping tissue therebetween;
a first cam member movable within the cartridge section to advance the first set of fasteners against the anvil to fully form the first set of fasteners, the first cam member movable in a first plane; and
a second cam member movable within the cartridge section along with the first cam member to advance the second set of fasteners to fully form the second set of fasteners, the second cam member movable in a second plane offset from the first plane and farther from the anvil section than the first plane when the anvil and cartridge sections are positioned to clamp tissue therebetween, wherein the first and second cam members are of substantially the same height and an overall height of the cam bar on first upper surface portion in the first plane is greater that an overall height of the cam bar on a second lower surface portion in the second plane,
wherein prior to firing, the plurality of fastener pushers are spaced apart from the first upper surface portion and second lower surface portion to engage the first and second cam bars, and wherein the fastener pushers spaced apart from the first upper surface portion have a height that is equal to a height of the fastener pushers spaced apart from the second lower surface portion.

12. The surgical fastener applying apparatus of claim 11, wherein the first set of fasteners has legs of a first length and the second set of fasteners has legs of a second longer length.

13. The surgical fastener applying apparatus as recited in claim 11, wherein the plurality of fastener pushers are configured to engage the fasteners as they are advanced by the cam bars.

14. The surgical fastener applying apparatus of claim 12, wherein the plurality of fastener pushers is configured to engage the first and second set of fasteners as they are advanced by the earn members, the plurality of fastener pushers being of substantially the same height.

15. The surgical fastener applying apparatus of claim 1, wherein each of the first upper surface portion and the second lower surface portion include a cam bar contacting surface and wherein the cam bar-contacting surfaces are on offset planes.

* * * * *